United States Patent [19]

Wason et al.

[11] 4,191,742
[45] Mar. 4, 1980

[54] AMORPHOUS PRECIPITATED SILICEOUS PIGMENTS AND METHODS FOR THEIR PRODUCTION

[75] Inventors: Satish K. Wason; Robert K. Mays, both of Havre de Grace, Md.

[73] Assignee: J. M. Huber Corporation, Locust, N.J.

[21] Appl. No.: 854,165

[22] Filed: Nov. 23, 1977

Related U.S. Application Data

[60] Division of Ser. No. 703,496, Jul. 8, 1976, Pat. No. 4,067,746, which is a continuation of Ser. No. 472,580, May 22, 1974, abandoned.

[51] Int. Cl.$^2$ ............................................... A61K 7/16
[52] U.S. Cl. ................................. 424/49; 106/288 B; 423/339
[58] Field of Search ................... 106/288 B; 423/339; 424/49

[56] References Cited

U.S. PATENT DOCUMENTS

| 3,928,541 | 12/1975 | Wason | 423/339 |
|---|---|---|---|
| 4,038,098 | 7/1977 | Wason | 106/288 B |

Primary Examiner—Winston A. Douglas
Assistant Examiner—J. V. Howard
Attorney, Agent, or Firm—Robert L. Price; Harold H. Flanders

[57] ABSTRACT

A method for producing precipitated silica products having a unique combination of physical and chemical properties is disclosed. The products are produced by acidulating a solution of an alkali metal silicate with an acid under carefully controlled precipitation conditions. In accordance with the method, at least a portion of the alkali metal silicate solution theoretically required to react with said acid is initially charged to the reaction vessel. Thereafter, the remaining silicate solution and the acid are simultaneously added to the reaction vessel in a manner to control the alkalinity of the reaction medium. By controlling the percent of the silicate solution initially charged to the reaction vessel, silicas having predetermined properties can be obtained. Properties of the products include low wet cake moisture content, low structure, low oil absorption, high abrasiveness, and low void volume. The products can be used as abrasive and polishing agents in dentifrice compositions. In one particular advantageous embodiment, an adduct material, such as aluminum, is added to control the refractive index of the product.

1 Claim, 2 Drawing Figures

AMORPHOUS PRECIPITATED SILICEOUS PIGMENTS AND METHODS FOR THEIR PRODUCTION

This is a division of application Ser. No. 703,496 now U.S. Pat. No. 4,067,746 filed July 8, 1976, which is a continuation of Ser. No. 472,580, filed May 22, 1974 now abandoned.

BACKGROUND OF THE INVENTION

1. Field of the Invention

The present invention relates to novel synthetic precipitated silicas and to a process for producing synthetic precipitated silicas having a new and unique combination of physical and chemical properties. More particularly, the invention relates to the production of amorphous, precipitated low structure silicas produced by reacting aqueous alkali metal silicate solutions with an acidification agent. The novel products produced by the method of the invention are low structure silicas having certain unique properties particularly with respect to structure index, oil absorption, void volume, and other physical properties. The novel low structure silicas are useful as abrasive and polishing agents in dentifrice compositions with the cleaning and the polishing characteristics thereof being superior to conventional dentifrice grade phosphate abrasives and other previously known silica gels, aluminas, and the like.

2. Description of the Prior Art

As known in the art, finely divided silicic acid or silica can be prepared by the acidulation of an aqueous silicate solution with an acid, such as sulfuric acid. Such products are commercially available and generally speaking are characterized by, and have, the following properties: high structure, high wet cake moisture content, high oil absorption, low valley abrasion, high surface area, and low pack density. Because of properties such as high oil absorption, the silicas have been widely and successfully used as reinforcing pigments in rubber. However, the high wet cake moisture content is disadvantageous in that the drying and filtration rates are increased. Further, the aforementioned properties of said known and commercially available silicas render then unsuitable for many uses. For example, while suitable as rubber reinforcing fillers, prior art silicas have no utility as cleaning and polishing agents in dentifrices. See German Pat. No. 974,958; French Pat. No. 1,130,627; British Pat. No. 995,351; Swiss Pat. No. 280,671; and U.S. Pat. No. 3,250,680.

As briefly noted above, there are a number of known techniques for preparing silica pigments which involve acidulating an aqueous silicate solution. Thus in U.S. Pat. No. 2,940,830 which issued June 14, 1960 to F. S. Thornhill, there is described a process for preparing finely divided silicas which are suitable as reinforcing agents in rubber compositions. Thornhill more specifically describes a process of preparing a silica material which is characterized by having an average ultimate particle size of 0.015 to 0.04 micron and a surface area of 25 to 200 square meters per gram by the controlled rate of addition of acid to an alkali metal silicate wherein the resultant slurry is constantly maintained at a pH above 7 in order to achieve the aforementioned end product characteristics. The Thornhill patent is specifically directed to the production of a product suitable as a reinforcing agent in rubber compositions.

In U.S. Pat. No. 3,235,331 which issued Feb. 15, 1966 to Nauroth et al, there is described a process for producing a precipitated silica which is also stated to be useful as a reinforcing agent for rubber. More specifically, this patent discloses a process wherein an aqueous alkali metal silicate solution and acid are simultaneously added to a reaction vessel. In the Nauroth et al patent, it is pointed out that this simultaneous addition is continued until the viscosity of the pool rises through a maximum and then falls to a substantially lower value. The amount of the acidification agent and the alkali metal silicate are proportioned so as to maintain the pH of the resulting slurry substantially constant throughout the major portion of the reaction and in the range of about 10 to 12. The process is generally conducted at a temperature of 80° to 90° C. and the end product, after drying, results in a silica which may have a surface area of 260 square meters per gram. The patentee points out that the product is satisfactory as a reinforcing agent for rubber.

In U.S. Pat. No. 3,445,189 issued May 20, 1969 to Maat et al, there is described a process for producing finely divided silicic acid by simultaneously adding solutions of an alkali silicate and a strong mineral acid to water at a temperature between 70° C. and 90° C. while maintaining the reaction pH between 7 and 9. The patentees point out that the product obtained by the aforementioned process is a finely divided non-gelatinous silicic acid which is useful as a filter for natural and synthetic rubber and other elastomers. It is also disclosed in this patent that for a silica to be useful as a filter for natural and synthetic rubber and other elastomers, its surface area and oil absorption are of vital importance. This patent further discloses that extensive investigations have further indicated that if a finely divided silicic acid is to have good reinforcing properties for rubber, it must have a surface area of 100 to 250 $m^2/g$ and an oil absorption or more than 2 cc/g or 200 cc/100 g. See column 2, lines 18 through 22.

In U.S. Pat. No. 3,730,749 which issued May 1, 1973 to James E. Morgan, there is disclosed a process for preparing silica for use in reinforcing compositions. It is pointed out in Morgan that the viscosity increase which occurs during the acidification or neutralization of aqueous alkali metal silicate is substantially minimized by adding a controlled amount of an akali metal silicate. In Examples I, II, and III of this patent, it is also noted that the silica filter cakes had solid contents of 18.5; 24.9; and 25.1 percent, respectively. This means that the percent wet cake moisture of the silicas disclosed in Examples I, II, and III is one hundred minus the percent solid content in the filter cake. In other words, the percent wet cake moisture (% WCM) of silicas mentioned in Examples I, II, and III is 81.5; 75.1; and 74.9, respectively. The surface area, the average ultimate particle sizes, and rubber data of silicas produced by the teachings of Examples II and III are listed in Table 3 which also sets forth that rubber compositions incorporating the silicas of Examples II and III have desirable rubber properties. It is further substantiated by this patent that rubber properties of silicas are related to the wet cake moisture of the silica pigment. A silica of high percent wet cake moisture and suitable particle size and surface area has better rubber properties than the corresponding material of lower wet cake moisture. Thus the silicas disclosed in Morgan have a higher structure index, and therefore the silicas are useful rubber reinforcing fillers.

From the above it will be seen that the structure index of a silica is related to the rubber properties—a silica of higher structure index will have better rubber properties than a silica of lower structure index. At this point, the various types of synthetic silicas, as well as "structure" and "structure index" should therefore be discussed.

In this regard, and as known in the art, commercially available synthetic silicas are derived either by a liquid phase or a vapor process. Silicas obtained by the vapor process are called fumed or pyrogenic silicas. Products obtained by the liquid process are categorized as silica gels and precipitated silicas. Thus, there are three distinct types of synthetic silicas on the market:

1. Pyrogenic Silicas

Pyrogenic or fumed silicas are prepared by reacting silicon tetrachloride vapor with oxygen and hydrogen gas at high temperatures. These products have high external surface areas and differ from other silicas (e.g., gels, precipitated silicas) prepared from the liquid phase process. Cabot and DeGussa are two suppliers of pyrogenic silicas.

2. Silica Gels

Silica gels are of two types—hydrogels and aerogels. Hydrogels are prepared by reacting a soluble silicate such as sodium silicate with strong sulfuric acid. The gel is washed salt-free, dried, steam micronized, and then classified. Aerogels are prepared from crude hydrogels by displacing its water content with an alcohol. The alcohol is then recovered by heating the gel in an autoclave.

Aerogels are lighter and fluffier than hydrogels because the shrinkage of the gel structure is avoided during the drying process. Gels have very large surface areas, generally in the range of 300–1,000 m$^2$/g and high porosities. Silica gels are offered, for example by W. R. Grace and Company under the trademark "Syloid"; by Monsanto under the trademark "Santocel"; and Glidden under the trademark "Silcron".

3. Precipitated Silicas

Precipitated silicas are produced by the de-stabilization and precipitation of silica from soluble silicate by the addition of a mineral acid and/or acidic gases. The reactants thus include an alkali metal silicate and a mineral acid, such as sulfuric acid or an acidulating agent such as $CO_2$.

When the acidification agent is added to the alkali metal silicate, at a certain point during the process, the silica starts precipitating. The addition of the acidification agent is continued until the $M_2O$ of the alkali metal silicate (M being the alkali metal) of the ultimate silica is less than about 1% by weight. Thus, as a general rule, the acidification agent is added to the alkali metal silicate to neutralize the alkali portion bound to the silicate anion. The reaction slurry is filtered and washed free of reaction by-product, which is the alkali metal salt of the acidification agent. The filter cake is dried and milled to obtain a silica of desired degree of fineness.

Prior to the drying step, the silica filter cake generally results in a filter cake which contains a surprisingly high amount of water. For example, a silica which is useful as a filler for reinforcement of rubber and elastomers generally contains 80% to 85% water in its cake. For example, see Example No. I, U.S. Pat. No. 3,730,749 where the percent wet cake moisture is 81.5. The percent water present in the filter cake is known as percent wet cake moisture or generally abbreviated as "% WCM."

One hundred minus the % WCM gives the solid content of the filter cake, i.e., the amount of silica which can be recovered in the solid form upon drying the filter cake. The percent solid content of the filter cake is termed percent filter cake solids and generally abbreviated as "% FCS." Thus, % WCM and % FCS are related by the equation:

$$\% \, WCM = 100 - \% \, FCS$$

or $$\% \, FCS = 100 - \% \, WCM$$

If we know the value of % WCM, we can calculate % FCS or vice versa.

Thus, a silica filter cake having 85% WCM will have 100 minus 85 or 15% FCS. This means that 15 pounds of silica can be recovered from such a filter cake by evaporating or drying 85 pounds of water from hundred pounds of filter cake. The total weight of filter cake consists of water and solid silica. In the example where the % WCM is 85, one can recover only 15 pounds of solid silica as can be seen below:

$$100 \text{ pounds filter cake} = 85 \text{ pounds water} + 15 \text{ pounds dry silica}$$
$$= 85\% \, WCM + 15\% \, FCS$$

Thus, there are 85 pounds of water associated with 15 pounds of solid silica content or $(85/15) \times 100 = 567$ pounds of water per 100 pounds of solid silica.

The water associated with the silica content of filter cake is structural water. This water is present whereby it occupies the available space between the silica aggregates and also the space inside the silica aggregates. As used herein, the term "structure" is defined as the ability of a silica to hold water in its wet cake. When silicas, such as the aforementioned known prior art products, hold a high percentage of water, i.e., from about 70 to 85%, they are known as high structure silicas. Materials holding less than 70% or from about 50 to 70% are referred to as low structure silicas. This total structural water content is a very important property of silica and is directly related to the functional and end use properties of silica. The amount of total structural water associated with 100 pounds of solid silica content of the filter cake is defined as "structure index" and abbreviated as S. I.

Mathematically, structural index (S. I.) of silica can be calculated if either the % wet cake moisture (WCM) or the % filter cake solid (FCS) values of said silica are known:

$$S.\,I. = \left( \frac{\% \, WCM}{100 - \% \, WCM} \right) \times 100 = \frac{\% \, WCM}{\% \, FCS} \times 100$$

Structure index of silicas in wet cake moisture range of 80–85% is listed in Table I.

Table I

Structure Index of Silicas With % WCM of 85–80

| % WCM | 100 − % WCM | S.I. |
|---|---|---|
| 85 | 15 | 567 |
| 84 | 16 | 525 |
| 83 | 17 | 488 |
| 82 | 18 | 455 |
| 81 | 19 | 426 |

Table I-continued

| Structure Index of Silicas With % WCM of 85–80 | | |
|---|---|---|
| % WCM | 100 − % WCM | S.I. |
| 80 | 20 | 400 |

Prior art precipitated silicas such as disclosed in the aforementioned patents (see U.S. Pat. Nos. 2,940,830; 3,235,331; 3,445,189; 3,730,749) are high structure silicas having high S. I. values. As stated, these silicas are useful as reinforcing fillers in elastomers and rubber.

SUMMARY OF THE INVENTION

In summary, the present invention relates to the production of novel synthetic precipitated silicas and to a new and unique process for producing precipitated silicas having certain unique properties.

The silicas of the instant invention are low structure silicas meaning thereby that low S. I. (Structure Index) values. While the prior art silicas are useful as reinforcing agents, the silicas of the present invention are unsuitable as reinforcing fillers. The low structure silicas of the instant invention are unique and belong to a new class of silica compounds. Thus the novel silicas of the invention are useful polishing and cleaning agents in dentifrices. Known silicas, which are useful reinforcing fillers, have no utility as cleaning and polishing agents in dentifrices. In this regard, it is disclosed in U.S. Pat. No. 3,538,230 that known amorphous silicas such as precipitated silicas, pyrogenic silicas, and aerogels are unsuitable for dentifrice use because of their initial small particle size and because of the ease in which they break down into small particle sizes which results in poor cleaning properties. Reinforcing silicas have high structure and possess good thickening properties but unacceptable abrasion, cleaning, and polishing properties. On the other hand, the silicas of the invention are very effective and useful in dentifrices as abrasives and exhibit superior cleaning and polishing properties than the conventional phosphates, calcium carbonate, and alumina dentifrice grade abrasives.

Stated broadly, the novel method of the invention is based on the discovery that if the addition of the acid to the silicate solution is carefully controlled, the resulting precipitated silicas possess the aforementioned unique combination of properties. More particularly, the method embodies the concept and discovery that if the alkalinity of the reaction medium, during the acidulation of the silicate solution, is closely controlled and maintained at a level higher than that of the initial silicate solution, the aforenoted new class of silicas are formed. As used herein, the term alkalinity is defined as the amount, in grams or mols, of the $Na_2O$ (if sodium silicate is employed) bound or associated with the silicate anion. It should be expressly understood that this is to be distinguished from the pH of the reaction mass. For example, in several of the patents referred to hereinabove, the pH of the reaction mass is held constant. In the instant invention, the pH decreases. In the practice of the method of the invention, and again broadly speaking, an initial portion of the total silicate theoretically required to react with the acid is charged to a reaction vessel. Thereafter the acidulating agent or acid and the remaining portion of alkali metal silicate solution are simultaneously added to the silicate solution initially charged to the reactor. As to be discussed in more detail hereinafter, the rates or ratio of the addition of the silicate and acid solutions are controlled or proportioned so that at any point in time (during the simultaneous addition of said acid and silicate solutions) the total alkalinity is higher than the alkalinity of the silicate solution initially charged to the reaction vessel, i.e., in the reaction medium at zero time. After the total silicate solution has been added, the acid addition is continued to complete precipitation of the new class of silica products of the invention. In accordance with a further method embodiment, the acidulating agent, such as sulfuric acid, is pre-mixed with an adduct such as aluminum (which is preferably added as a water soluble salt thereof, as, for example, aluminum sulfate). It has been found that the addition of the adduct, coupled with the concept of the precipitation technique of the present invention, controls the refractive index of the resulting silica.

As will be seen from the above, the precipitated silicas produced in accordance with the invention results in silica products which have a unique balance of physical, chemical properties as compared to conventionally precipitated silicas.

It is accordingly a general object of the present invention to provide a novel process for producing precipitated silicas having new physical and chemical properties.

Another and more particular object is to provide a unique process for producing synthetic amorphous precipitated siliceous products which have particular utility for use as abrasive and polishing agents in dentifrice compositions.

Yet another object is to provide a highly effective and improved process for producing a silicic acid product which exhibits lower wet cake moisture or higher percent solids and which has high abrasion values and low oil absorption characteristics.

Yet still another object is to provide novel synthetic amorphous precipitated siliceous products which are useful as abrasion and cleaning agents in clear toothpaste compositions.

A still further object is to provide a process for producing low structure, low wet cake moisture, controlled surface areas, low oil absorption, high abrasion and high pack density precipitated silicic acid products.

BRIEF DESCRIPTION OF THE DRAWINGS

The manner in which the foregoing and other objects are achieved in accordance with the present invention will be better understood in view of the following detailed description and accompanying drawings, which form a part of the specification and wherein.

DESCRIPTION OF PREFERRED EMBODIMENT(S)

Figure 1:
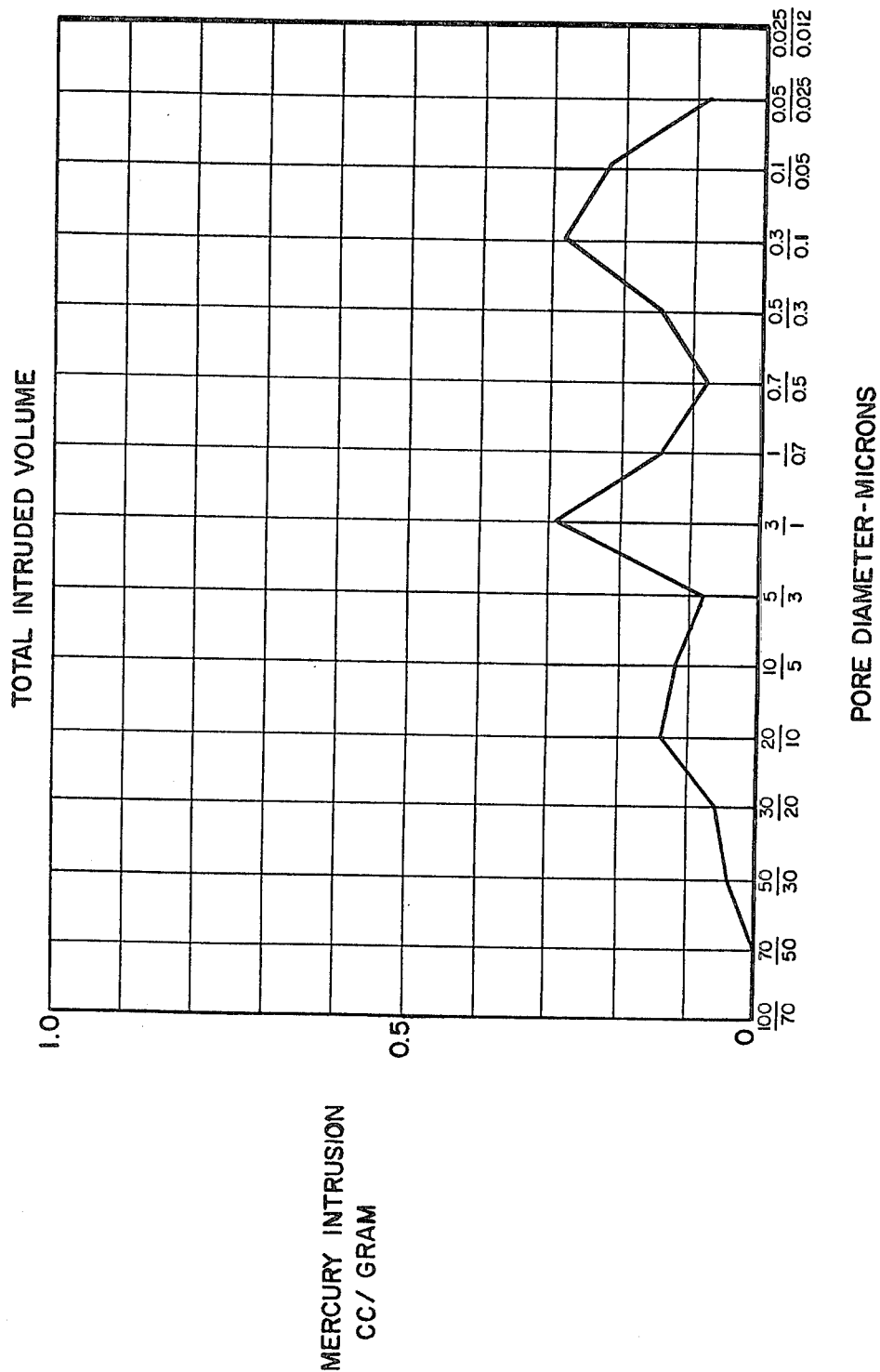
FIG. 1 is a graph illustrating a typical void size (structure) distribution of the new low structure silicas of the invention.

As briefly discussed above, the present invention is directed to the production of a new class of silicas known as low structure silicas which are distinctly different from the prior art silicas. Prior art silicas have characteristics which make said silicas useful reinforcing fillers. Silicas of the instant invention are unsuitable as reinforcing fillers because of their low structure index values. The present invention provides a novel process for producing low structure silicas. In the prior art processes for producing silicas, it is disclosed that during the precipitation process, the reaction medium goes through a maximum viscosity. Apparently, this increase in viscosity is essential for producing reinforcing silicas of high structure index values. In the present invention, the low structure silicas are produced by the acidification of alkali metal silicate under carefully controlled conditions. There is no substantial increase in viscosity throughout the entire process of producing the said novel low structure silicas. The alkalinity of the reaction mass is controlled throughout the process of producing low structure silica such that the final alkalinity is higher or greater than the initial value at the beginning of the reaction, namely, on the order of from 20 to 500% or higher.

The process of the invention may be summarized as follows:

(a) Simultaneously adding an alkali metal silicate solution and an aqueous solution of a mineral acid to an agitated reaction medium containing a desired level of alkali metal silicate to provide the needed alkalinity.

(b) The alkali metal silicate and the mineral acid rates are so proportioned to provide a controlled gradual increase of effective alkalinity during the process and (c) Simultaneous feeding of the silicate is continued until the final alkalinity is substantially higher than the initial alkalinity present in the reaction medium at zero time and (d) The reaction temperature is maintained between 50° C. to 90° C. throughout the entire process and the acidification continued after stopping the silicate addition to maintain a reaction slurry pH of less than 6.0.

(e) The quantity of silicate and acid used is preferably such that the resulting slurry, after all additions have been made thereto, contains from about 30 to less than 12% by weight of $SiO_2$, and preferably from about 4% to about 8% by weight of $SiO_2$.

(f) The reaction slurry is filtered, washed free of reaction by-product, dried, and milled to desired degree of fineness.

The alkali metal silicate used should normally have the composition $M_2O \cdot (SiO_2)_X$ where M is an alkali metal and X is 2 or above, usually 2 to 4 including the fractional numbers. Sodium or potassium silicates and other alkali metal silicates can be used, but sodium silicate is preferred because it is most economical. Several mineral acids and other weak acidification agents like $CO_2$ and organic acids may be employed in the practice of the invention. Examples of mineral acids which have been found especially suitable include phosphoric, nitric, hydrochloric, and sulfuric acid. Of these, hydrochloric acid and sulfuric acid are preferred; and sulfuric acid is particularly preferred because it is the most economical mineral acid to use. If the mineral acid is a dibasic acid, i.e., sulfuric, the concentration of the acid solution should be on the order of from 8 to 22% and preferably from about 10 to 15% by weight. Other acids, such as mon- or tri-basic acids should have their concentration adjusted to normalities (N) equivalent to the dibasic acid. It is believed that the low mineral acid concentration helps to minimize localized reactions at high concentrations of the alkali metal silicate solution and is preferred for producing low structure silicas. Furthermore, in order to minimize the effects of localized high-acid concentrations, it is preferred that the alkali metal silicate solution and the mineral acid solution be introduced in diametrically opposed parts of the aqueous slurry in order to be quickly diluted with the reaction mixture before localized reactions between high concentration of the acid and silicate occurs. Stated differently, the silicate and acid solutions are preferably added to different parts of the reaction slurry body in order to avoid reaction between localized high concentrations of silicate and acid.

The alkali metal silicate solution and the aqueous solution of a mineral acid are simultaneously added under controlled rates over an extended period of time to the reaction medium containing a desired level of alkali metal silicate to provide the needed alkalinity at the onset of the reaction. The rate of increase of alkalinity, i.e., the $Na_2O$ content of the reaction medium is controlled per unit time so that when the silicate addition is stopped, the total alkalinity at that point is significantly higher than the alkalinity present in the reaction medium at zero time. The silicate addition is conducted along with the acidification agent for a period of from about 55 to 90% ($t_m$) of the total reaction time ($t_f$), the latter being from about 20 minutes to 4 hours.

Turning now to further specific details, in the practice of the invention, a predetermined portion of the total alkali metal silicate to be employed in the reaction (i.e., theoretically required to react with the acid) is first charged to a reactor as a solution thereof and the solution is heated to a temperature in the range of from about 50° C. to 90° C., preferably on the order of from about 70° to 90° C. with continuous agitation. The initial alkalinity of the silicate solution, i.e., the moles of $M_2O$ (M=alkali metal) bound to the silicate anion, must be at least 8.0 mol percent, based on the total weight of the alkali metal silicate theoretically required to react with the acid. For example, if 100 mols of the alkali metal silicate are required to react with the acid, then 8 mols of the silicate must be initially charged to the reaction vessel. The concentration of the alkali metal silicate solution may be in the range of from about 8 to 25% by weight silicate, preferably from about 8 to 15% by weight silicate. The predetermined mol percentage of the predetermined cumulative total of the alkali metal silicate, i.e., that which is initially charged to the reaction vessel, may comprise an amount of at least 8 mol percent (as stated above) up to an amount not greater than 50 percent.

The acidulating agent or acid, e.g., sulfuric acid, and the remaining portion of the solution of the alkali metal silicate are next simultaneously charged to the reaction vessel in a manner and at a rate such that alkalinity of the reaction mass increases. In this regard, the solutions of the silicate and acid are added at a rate to provide a controlled increase of the alkalinity such that the maximum alkalinity produced upon completion of the addition of the total quantity of the alkali metal silicate at the time of maximum of alkalinity, defined as $t_m$, is from 20% to 500% higher than the initial alkalinity of the predetermined mol percentage of the cumulative total of the predetermined quantity of the alkali metal silicate to be charged to the reaction vessel at the inception of the reaction. Products having particularly unique properties are produced when the alkalinity is increased such that the maximum alkalinity is from 250 to 500% higher than the initial alkalinity.

After the total alkali metal silicate has been added to the reactor, i.e., the amount theoretically required to react with the acid, the addition of the acid is continued to complete the precipitation and to reduce the pH of the aqueous reaction mass to less than 6.0. An excess of the acid may be employed if required. However, in the practice of the invention, this has not been found to be necessary. After the addition of the reactants, the reaction mass should contain from about 3 to 12% by weight of $SiO_2$. Throughout the reaction and precipitation of the $SiO_2$, the reaction mass is maintained at a temperature of between about 50° to 90° C. and preferably at 70° to 90° C. At the completion of the reaction, the reaction mass is filtered and the wet filter cake comprising the silicon dioxide produced is recovered. The filtered mass or cake is then washed (to remove reaction soluble salts, such as sodium sulfate), dried, and ground or milled.

In accordance with the invention, and a remarkable concept and discovery, lies in the fact that by varying the amount of the silicate solution initially introduced into the reaction vessel, a new class of low structure silicas having a wide range of predetermined properties can be obtained. For example, if the mol percentage of the portion of the predetermined cumulative total of the alkali metal silicate that is initially introduced into the said reaction vessel is from about 8% to 14% inclusive, the resulting product has a wet cake moisture of less than 66%, a structure index of less than 200, an oil absorption of less than 125 cc/100 grams, a void volume of from 1 to 2.55 cc Hg/gram of $SiO_2$ inclusive, and a BET surface area of from 65 to 375 square meters per gram. When the initial mol percentage is from 14 to 35%, the product has a wet cake moisture of from 66% to 76% inclusive, a structure index of from 200 to 354, an oil absorption of from 125 to 175 cc/100 grams, a void volume of from 2.55 to 4.0 cc Hg/gram of $SiO_2$, and a BET surface area of from 80 to 200 square meters per gram.

From the above it will be seen that the process of the instant invention results in a new class of products having a unique combination of physical and chemical properties. These include, e.g., an oil absorption in the range of from 75–180 cc/100 grams; a structure index of less than 354 and in the range of from 125–354; a BET surface area of 65 to 375 square meters per gram; a wet cake moisture (of the filter cake) in the range of from 55 to 76% and void volumes of from 1 to 4.1. As previously discussed, in one method embodiment the refractive index of the precipitated product can be controlled by the addition of an adduct element (such as aluminum, mangnesium, and the like) to provide an abrasive or polishing agent for a clear translucent or transparent toothpaste composition. Thus in this embodiment, the acid is premixed with a solution of the adduct material, i.e., aluminum (preferably in the form of a water soluble salt such as aluminum sulfate, etc.) and the acid-metal salt mixture is then used for acidulating the aqueous alkali metal silicate solution. It has been found that the addition of the adduct may increase the surface area of the product but does not affect the other properties thereof.

In the practice of the invention, improved and very important processing advantages are also obtained. While particular embodiments have been disclosed for illustrative purposes, the invention is not intended to be limited thereto. For example, a product can be easily produced for a special utility. Also, and as should be readily appreciated by those skilled in the art, no special equipment is required in the method herein described. In this regard, the reactor or reaction vessel should be equipped with heating means, e.g., a steam jacket, in order to maintain the desired reaction temperature and should have adequate agitation means to produce a strong backflow on the body of the liquid and to avoid zones of high concentration of the incoming reactants. Storage vessels (for the reactants) connected to the reaction vessel through lines fitted with flow control means may also be provided. The reaction vessel may be equipped with an outlet line leading to a filter which may be of conventional design. As noted above, the filtered mass is washed and dried. Such steps may also be conducted in conventional equipment.

The following Examples will serve to further illustrate the present invention, but it should be expressly understood that they are not intended to limit it thereto.

EXAMPLE I

Into a 151 liter stainless steel reactor jacketed for steam heating was added 6.8 liters of sodium silicate solution (3.78 percent $Na_2O$, 9.52 percent $SiO_2$) of specific gravity 1.121 containing 42 grams of $Na_2O$ per liter. The initial alkalinity of the reaction medium at zero time was 285.6 grams $Na_2O$. The reaction medium was heated to 88° C. with continuous agitation. At this point sulfuric 10% concentration (specific gravity 1.066) and sodium silicate solution were added simultaneously to the reaction medium at the rate of 550 ml/min. acid and 1330 ml/min. sodium silicate while maintaining the reaction temperature at 88° C.±1° C. These two solutions were added to the reaction medium over an extended period of time as shown in Table II. At a point when the total alkalinity ($Na_2O$ portion of silicate) in the reaction medium was at least by a factor two higher than its initial value in the reaction medium, the silicate solution was turned off (see Table II) but acid addition was continued until the slurry pH was below 6.0. The reaction slurry was boiled at 100° C. for twenty minutes and the reaction pH was adjusted again below 6.0. The resulting slurry contained 6% $SiO_2$ and was filtered, washed free of reaction by-product (sodium sulfate) and the filter cake was recovered. A portion of the filter cake was dried at 105° C. until constant weight to determine the percent wet cake moisture and percent filter cake solid content of the low structure silica. The remainder of the silica was dried in the oven and dry material milled to the desired degree of fineness. The dry silica was subjected to various physical-chemical tests and the following data was obtained:

% WCM = 65.1
Structure Index = 186.5
Oil Absorption = 96 cc/100 gram
Void Volume = 1.67 cc Hg/gram silica
BET Surface Area = 230 square meters per gram The structure index was calculated by using the following equation:

$$S. I. = \left( \frac{\% \ WCM}{100 - \% \ WCM} \right) \times 100$$

The specific surface area of the end product was determined by the nitrogen absorption method described by Brunauer, Emett, and Teller (BET) in the "Journal of the American Chemical Society," Volume 60, p. 309, published in 1938.

The oil absorption of the end product produced from Example I was determined by the rub-out method. This is based on a principle of mixing linseed oil with a silica by rubbing with a spatula on a smooth surface until a stiff putty-like paste is formed. By measuring the quantity of oil required to give a paste mixture which will curl when spread out, one can calculate the oil absorption value of the silica—a value which represents the volume of oil required per unit weight of silica to saturate the silica sorptive capacity. Calculation of oil absorption value was done as follows:

$$\text{Oil Absorption} = \frac{\text{cc oil absorbed} \times 100}{\text{weight of sample, grams}}$$
$$= \text{cc oil}/100 \text{ gm silica}$$

The void volume of silica was determined by using the Aminco-Winslow Porosimeter. This instrument is a completely hydraulic machine used to measure the void structure of various materials. The mercury is forced into the voids as a function of pressure and the volume of mercury displaced per gram of sample is calculated at each pressure setting. Increasements in volume (cc/g) at each pressure setting are plotted against the void size increasements corresponding to the pressure setting increasements. The following data was collected for the low structure silica of Example I (Table IIa).

Table II

| Time, min. (cumulative) | Sodium Silicate added, liters (cumulative) | $H_2SO_4$ added liters (cumulative) | Moles $Na_2O$ (cumulative) | % Alkalinity (cumulative) |
|---|---|---|---|---|
| 0 | 6.80 | 0 | 4.62 | 100.0 |
| 5 | 13.45 | 2.75 | 6.15 | 133.1 |
| 10 | 20.10 | 5.50 | 7.67 | 166.0 |
| 15 | 26.75 | 8.25 | 9.20 | 199.1 |
| 20 | 33.40 | 11.00 | 10.72 | 232.0 |
| 25 | 40.05 | 13.75 | 12.24 | 264.9 |
| 30 | 46.70 | 16.50 | 13.77 | 298.0 |
| 35 | 53.35 | 19.25 | 15.30 | 331.2 |
| 40 | 60.00 | 22.00 | 16.82 | 364.1 |
| 45 | 66.65* | 24.75 | 18.34 | 397.0 |
| 50 | | 27.50 | 15.34 | 332.0 |
| 55 | | 30.25 | 12.35 | 267.3 |
| 60 | | 33.00 | 9.35 | 202.4 |
| 65 | | 35.75 | 6.35 | 137.4 |
| 70 | | 38.50 | 3.35 | 72.5 |
| 75 | | 41.25 | 0.35 | 7.6 |
| 75.5 | | 41.53 | 0.05 | 1.1 |

*Silicate solution was turned off. As can be seen, the cumulative alkalinity, at this point, is 397% of initial value in the reaction medium.

Table IIa

| Pressure Gage PSIG | Pore Diameter (Microns) | Cumulative Intruded Volume (cc/g) | Intruded Volume (cc/g) |
|---|---|---|---|
| | 100 | 0.00 | 0.00 |
| | 70 | 0.00 | 0.00 |
| | 50 | 0.00 | 0.00 |
| | 30 | 0.04 | 0.04 |
| | 20 | 0.10 | 0.06 |
| 6.6 | 10 | 0.24 | 0.14 |
| 24 | 5 | 0.36 | 0.12 |
| 46 | 3 | 0.44 | 0.08 |
| 163 | 1 | 0.73 | 0.29 |
| 238 | 0.7 | 0.87 | 0.14 |
| 341 | 0.5 | 0.95 | 0.08 |
| 572 | 0.3 | 1.09 | 0.14 |
| 1746 | 0.1 | 1.37 | 0.28 |
| 3488 | 0.05 | 1.59 | 0.22 |
| 7000 | 0.025 | 1.67 | 0.08 |

The above data suggests that voids of sizes between 0.025 microns and 30 microns exist in the end product of Example I. The total volume of the void is 1.67 cc mercury/gram of sample. For functional performances in dentifrices, the end product should have as low total void volume as possible. Commercially available reinforcing silica fillers produced by the above-noted prior art processes have total void volume in excess of 4.5 cc Hg/gram of silica. Void size distribution for silica of this instant invention is depicted in FIG. 1, and is definitely by several factors lower than the conventional prior art silicas.

EXAMPLE II

The procedures of Example I were repeated except the following changes were made: A silicate solution of 1.30 specific gravity and of composition of 8.9% $Na_2O$ and 28.7% $SiO_2$ was diluted with enough water to prepare a dilute silicate solution of 1.101 specific gravity (and composition, 2.98% $Na_2O$, 9.62% $SiO_2$). This silicate solution was used as a reaction medium and contained 32.8 grams $Na_2O$ per liter. Sulfuric acid used had a concentration of 11.4% and specific gravity of 1.076 at 20° C. In this example a mixed acidification agent was used by adding seven volumes of 15.4% aluminum sulfate of specific gravity 1.092 with one hundred volumes of sulfuric acid. The mixed acidification agent was simultaneously added with silicate to the reaction medium which contained 7.57 liters of sodium silicate of specific gravity 1.101. The rate of acid addition was 613 ml/min. and silicate 1,480 ml/min. The silicate addition was so proportioned that the alkalinity at the point of silicate addition termination was at least 120% higher than the initial alkalinity in the reaction medium. The reaction temperature and the other processing parameters were similar to Example I. The rate of addition of two solutions to the reaction medium and the change of alkalinity as a function of time are listed in Table III.

The end product obtained from this experiment was tested for various physical-chemical properties which were as follows:

% WCM = 66.6
Structure Index = 199.4
Oil Absorption = 118
Void Volume = 2.55
BET Surface Area = 175

Table III

| Time, min. (cumulative) | Sodium Silicate, added liters (cumulative) | H2SO4 added liters (cumulative) | Moles Na2O (cumulative) | % Alkalinity (cumulative) |
| --- | --- | --- | --- | --- |
| 0 | 7.57 | 0.00 | 4.00 | 100.0 |
| 5 | 14.97 | 3.06 | 4.10 | 102.5 |
| 10 | 22.37 | 6.12 | 4.18 | 104.5 |
| 15 | 29.77 | 9.18 | 4.27 | 106.7 |
| 20 | 37.17 | 12.24 | 4.33 | 108.2 |
| 25 | 44.57 | 15.30 | 4.45 | 111.2 |
| 30 | 51.97 | 18.36 | 4.54 | 113.5 |
| 35 | 59.37 | 21.42 | 4.63 | 115.7 |
| 40 | 66.77 | 24.48 | 4.72 | 118.0 |
| 45 | 74.17* | 27.54 | 4.81 | 120.2 |
| 50 | | 30.60 | 0.99 | 24.7 |
| 51 | | 31.21 | 0.23 | 5.7 |

*-Silicate addition was discontinued

EXAMPLE III

A further experiment was conducted similar to the general procedure of Example II except to the reaction medium was added 7.57 liters of sodium silicate solution of 1.138 specific gravity and composition of 3.69% Na2O and 11.89% SiO2. The reaction medium was heated to 80° C. with continuous stirring. The initial concentration of total alkalinity in the reaction medium was 41.9 grams Na2O per liter. Silicate and acid solutions were added to the reaction medium at the rate of 1480 ml/min and 613 ml/min respectively. The silicate addition was stopped when the alkalinity during the process increased to 308% of its initial value in the reaction medium. The acidification agent was added until the alkalinity at the end of the batch dropped below 4% of the initial alkalinity present in the reaction medium. The end product of this Example was evaluated for various physical-chemical properties with the following data being obtained:
% WCM=61.4
Structure Index=159
Oil Absorption=90
Void Volume=2.16
BET Surface Area=373

The data obtained in the experimental set up of Example III is listed in Table IV.

Table IV

| Time, min. (cumulative) | Sodium Silicate added (liters cumulative) | H2SO4 added (liters cumulative) | Moles Na2O (cumulative) | % Alkalinity (cumulative |
| --- | --- | --- | --- | --- |
| 0 | 7.57 | 0 | 5.15 | 100.0 |
| 5 | 14.97 | 3.07 | 6.34 | 123.1 |
| 10 | 22.37 | 6.14 | 7.53 | 146.2 |
| 15 | 29.77 | 9.21 | 8.73 | 169.5 |
| 20 | 37.17 | 12.28 | 9.93 | 192.8 |
| 25 | 44.57 | 15.35 | 11.12 | 215.9 |
| 30 | 51.97 | 18.42 | 12.31 | 239.0 |
| 35 | 59.37 | 21.49 | 13.51 | 262.3 |
| 40 | 66.77 | 24.56 | 14.70 | 285.4 |
| 45 | 74.17 | 27.63 | 15.90 | 308.7 |
| 50 | | 30.70 | 12.06 | 234.2 |
| 55 | | 33.77 | 8.23 | 159.8 |
| 60 | | 36.84 | 4.39 | 85.2 |
| 65 | | 39.91 | 0.55 | 10.7 |
| 65.5 | | 40.22 | 0.16 | 3.1 |

EXAMPLE IV

This experiment was conducted similar to that of Example III except that in this test 7.57 liters of sodium silicate of 1.120 specific gravity and of 4.52% Na2O and 8.74% SiO2 composition was added to the steam jacketed reactor as a reaction medium. The concentration of Na2O in grams per liter in the reaction medium was 50.6. The solution was agitated continuously at the reaction temperature of 80° C. Both the silicate and acid solutions were added simultaneously to the reaction medium. The sulfuric acid was premixed with 15.4% aluminum sulfate solution in the ratio of 100:7 by volume prior to simultaneously adding it with silicate to the reactor. The silicate addition was discontinued when the final alkalinity just prior to discontinuing the silicate was at least 400% of the initial alkalinity present in the reaction medium. The end product from this experiment was evaluated for physical-chemical properties with the data being listed below.
% WCM=56.2
Structure Index=128.3
Oil Absorption=80
Void Volume=1.63
BET Surface Area=303

The rate at which the alkalinity changed every five minutes during the entire process is listed in Table V.

Table V

| Time, min. (cumulative) | Sodium Silicate added (liters cumulative) | H2SO4 added (liters cumulative) | Moles Na2O (cumulative) | % Alkalinity (cumulative |
| --- | --- | --- | --- | --- |
| 0 | 7.57 | 0 | 6.21 | 100.0 |
| 5 | 14.97 | 3.07 | 8.44 | 135.9 |
| 10 | 22.37 | 6.14 | 10.66 | 171.7 |
| 15 | 29.77 | 9.21 | 12.90 | 207.7 |
| 20 | 37.17 | 12.28 | 15.13 | 243.6 |
| 25 | 44.17 | 15.35 | 17.03 | 274.2 |
| 30 | 51.97 | 18.42 | 19.59 | 315.4 |
| 35 | 59.37 | 21.49 | 21.82 | 351.4 |
| 40 | 66.77 | 24.56 | 24.05 | 387.3 |
| 45 | 74.17 | 27.63 | 26.28 | 423.2 |
| 50 | | 30.70 | 22.44 | 361.3 |
| 55 | | 33.77 | 18.61 | 299.7 |
| 60 | | 36.84 | 14.77 | 237.8 |
| 65 | | 39.91 | 10.93 | 176.0 |
| 70 | | 42.98 | 7.09 | 114.2 |
| 75 | | 46.05 | 3.26 | 52.5 |
| 78 | | 47.89 | 0.54 | 8.7 |

Figure 2:
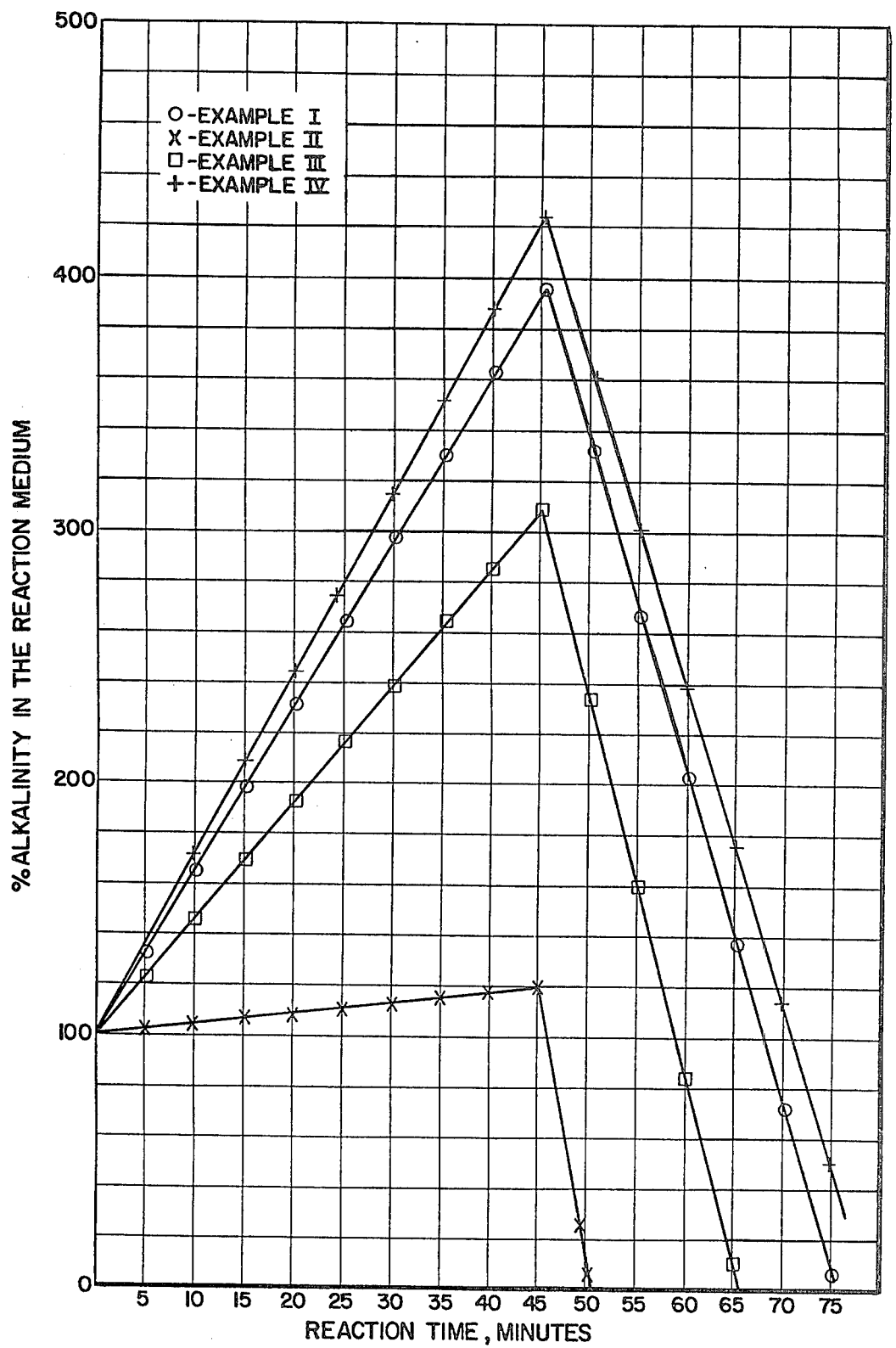
FIG. 2 is a graph showing the percent cumulative alkalinity as a function of time in the practice of the method of the instant invention.

From the above it will be seen that the novel and unique product of the instant invention can be produced by controlling the ratio of the final to the initial alkalinity in the reaction medium. How this alkalinity changes as a function of reaction time is shown by FIG. 2 wherein data collected in Examples I through IV has been plotted. From FIG. 2 it can be readily seen that a product of higher structure index is obtained when the ratio of final to the initial alkalinity in the reaction medium is relatively lower. Stated differently, a product of lower structure index can be readily produced by following the teachings of the present invention if the ratio of final to the initial alkalinity in the reaction medium is maintained relatively very high. For example, in Example No. IV, the maximum final alkalinity was 423.2 percent versus 100% initial alkalinity in the reaction medium. This ratio as obtained in Example IV is considered very high and as stated previously a process in which the alkalinity ratio is maintained high, results in an end product of relatively lower structure index. This is substantiated by the fact that structure index in Example IV was very low and to be exact it was 128.3. In Example II, the final alkalinity to initial alkalinity ratio in the reaction medium at a point when the silicate addition is discontinued is relatively low. The maximum alkalinity reached only 120.2% of its initial value. Therefore, the end product from Example II has relatively higher structure index than end product of Example IV. The structure index of silica produced in Example II is 199.4.

Structure Index as a Function of Silicate Concentration in the Reaction Medium

In a series of further tests, the general procedures of Examples I–IV were repeated except that the percent of total silicate solution charged to the reaction vessel was varied. It was established that structure index of silicas can be varied by varying the percent silicate in the reaction medium at zero time. The silicate used in these tests had a specific gravity of 1.16 and composition of 4.98% $Na_2O$ and 13.02% $SiO_2$. The silicate solution contained 57.8 grams of $Na_2O$ per liter. The sulfuric acid solution used had a concentration of 14% and specific gravity of 1.106. The addition of silicate and acid to the reaction medium was so proportioned that the alkalinity change per unit time was controlled within the desired limits. The further processing parameters were similar to those described in Examples I through IV. The results of these tests are shown in Table VI.

Table VI

| Example No. | % Silicate in RXN Medium | % WCM | S.I. | Oil Absorption | Void Volume | BET Surface Area |
|---|---|---|---|---|---|---|
| V | 10 | 61.1 | 157.1 | 95 | 1.84 | 65 |
| VI | 15 | 68.2 | 214.5 | 144 | 2.65 | 191 |
| VII | 20 | 70.4 | 237.8 | 151 | 2.87 | 138 |
| VIII | 30 | 72.3 | 261.0 | 160 | 3.11 | 126 |
| IX | 35 | 75.2 | 303.2 | 175 | 3.96 | 141 |
| X | 13 | 65.8 | 192.4 | 109 | 2.01 | 364 |
| XI | 9 | 55.7 | 125.7 | 87 | 1.53 | 114 |
| XII | 50 | 78.0 | 354.0 | 180 | 4.10 | 200 |

The particle size measurement of the product of the invention was conducted by using the MSA particle size analysis technique and equipment. It is a sedimentation method that is based on Stoke's Law. Stoke's Law relates settling velocity to particle size according to the following equation:

$$t = \frac{18.37 \times 10^8 \, U_o \, h}{(p - p_o) \, g \, d^2}$$

where
t = time in seconds to settle a distance h in cm
$U_o$ = absolute viscosity (poise) of the settling liquid
p = particle density, g/cc
$P_o$ = settling liquid density, g/cc
d = particle size, microns
g = gravitational constant, 980 cm/sec This equation shows that the time to settle a given distance is inversely proportional to the square of the particle size and is a function of the liquid viscosity and the particle and liquid densities. The MSA technique uses both gravity and centrifugation for settling particles. Centrifugation is used for the fine particles in order to have a reasonable time for the operation. For example, it requires 24 hours for a one micron particle of 2.7 density to settle 10 cm in water.

For particle size determinations, MSA uses a combination of time with one of four special constant speed centrifuges (300, 600–1200, 1800, and 3600 rpm). Special centrifuge tubes with small capillaries at the bottom are used. The height of the sediment in the capillary is measured using a special projector. The particle size distribution is calculated from the ratio of the sediment height at times corresponding to specific particle sizes to the height after all the particles are settled.

The data does not represent the ultimate particle size of materials. It represents the aggregate and/or agglomerate size distribution. In the MSA technique, 0.2 g material is dispersed in 100 ml of a 30/70 volume acetone/water mixture. The mixture used is a non-shear, counter-rotating stirrer. A small volume of this dispersion is then transferred to the sedimentation tube which contains distilled water.

The MSA size distribution data for end products produced in Examples I through VIII are listed in Table VII.

From Table VII, it will be seen that the particle size of the low structure silicas of the invention can be controlled by controlling the processing parameters as disclosed and discussed hereinabove.

As discussed above, the unique silicas of the invention may be advantageously employed as abrasive or polishing agents in toothpaste compositions. This is truly remarkable inasmuch as precipitated silicas of the prior art cannot be so employed. If the products of the invention are used in toothpaste compositions, and as known in the art, the dentifrice may contain, for example, humectant minerals and binders to give the dentifrice a smooth texture and good flowability. The above materials, as well as the specific formulations of toothpastes, are well known in the art and are disclosed for example in U.S. Pat. Nos. 2,994,642 and 3,538,230 and numerous publications. A further detailed disclosure of dentifrice formulations is given in U.S. Pat. No. 3,726,961.

Table VII

MSA PARTICLE SIZE DISTRIBUTION DATA
PERCENT BY WEIGHT LESS THAN SIZE

| Size (Microns) | Example No. | | | | | | | |
|---|---|---|---|---|---|---|---|---|
| | I | II | III | IV | V | VI | VII | VIII |
| 30 | 98 | 98 | 98 | 99 | 94 | 100 | 99 | 100 |
| 20 | 95 | 93 | 90 | 96 | 86 | 99 | 95 | 100 |
| 15 | 88 | 83 | 80 | 89 | 75 | 96 | 90 | 99 |
| 10 | 70 | 61 | 60 | 69 | 58 | 91 | 74 | 94 |
| 5 | 43 | 34 | 30 | 38 | 39 | 67 | 48 | 70 |
| 3 | 29 | 20 | 24 | 24 | 25 | 54 | 30 | 54 |
| 1 | 8 | 7 | 8 | 7 | 8 | 13 | 7 | 13 |
| 0.5 | 2 | 0 | 1 | 2 | 1 | 4 | 2 | 4 |
| 0.3 | 0 | 0 | 0 | 0 | 0 | 0 | 0 | 0 |

In this regard, dentifrice formulations have been produced, ranging from liquids are powders to the highly popular pastes or dental creams. Dental creams are the more difficult to compound successfully in that they require careful balancing of polishing agent, humectant, water, binder, preservatives, detergents, flavoring, sweeteners, and therapeutic agents to produce a smooth homogeneous paste.

Most modern dental cream formulations use one of several phosphate materials as the polishing agent. Examples of the phosphate polishing agents are dicalcium phosphate, anhydrous dicalcium phosphate, tricalcium phosphate, thermally converted dicalcium phosphate, and insoluble sodium metaphosphate. The amount of phosphate materials added to the dental formulations will range between about 5 percent and 60 percent by weight.

The most widely used humectants in toothpaste are glycerine and sorbitol. Propylene glycol is also used in small amounts and to a very limited extent. The primary function of humectant as part of the liquid phase is to retain moisture which provides good texture and maintains an attractive glossy appearance when the paste is exposed to air.

The binder employed therein is to prevent separation of the liquid and solid phases. The most conventionally used binders are the seaweed colloids and synthetic derivatives of cellulose, specifically Carrageenan and sodium carboxymethyl cellulose. Others such as gums have been used. Combinations of these binders have also been employed.

Since the natural and synthetic water dispersions of organic binders are subjected to microbial or mold attack, a relatively small amount of preservatives is added to the paste. Examples of preservatives used in the industry are the esters of parahydroxyl benzoates.

The function of the detergents within the dental formulation is to provide greater cleansing action due to the lowering of the surface tension and the sudsing action in the mouth. Among detergents used are sodium N-lauryl sarcosinate, sodium lauryl sulfate, sulfoculaurate, sodium alkyl sulfoacetate, and sodium dioctyl sulfosuccinate.

Since toothpaste flavoring probably represents the greatest single factor in consumer acceptance, great care has been employed in selecting balanced blends of different essential oils. These are rarely, if ever, used alone. Combinations of principal flavors are wintergreen, peppermint, and sassafras and are used with secondary oils such as pimento, clove, and anise.

Saccharin and sodium cyclamate are widely used to improve taste and enhance the flavor qualities of the toothpaste. The synthetic sweeteners may be used in combination to obtain optimum sweetness and absence of after-taste. Their desirable properties are obtained at very low concentrations and consequently they have negligible influence on the toothpaste consistency.

Since water is such a common element, it is important in obtaining stable toothpaste formulations to employ substantially pure water therein. It is common practice to demineralize the water that is employed.

The therapeutic agents within the dental creams are to prevent decay of the tooth and are commonly in the form of stannous fluorides and sodium fluoride material.

Difficulties have been encountered in using combinations of the above materials in modern dentifrice formulations. Specific scavenging of the fluoride ions by the phosphate and calcium containing polishing agents have been experienced. Thus, in formulating a dentifrice composition, a polishing agent must be selected to provide excellent polishing properties and have a very high degree of compatibility with the fluoride system and in particular should not scavenge the fluoride ion.

The products of the invention do not contain calcium and have a high degree of compatibility with fluoride compositions used in toothpaste. The degree of the abrasiveness of the polishing agent of the present invention can be controlled by controlling the structure index of silicas and particle sizes of said silica abrasives.

Thus according to the present invention, a new class of silica polishing agents have been discovered which have desired polishing and cleaning properties when formulated in a dentifrice composition.

In a series of tests the low structure silicas of Examples I through IV were formulated into a toothpaste having the following composition by weight:

| | |
|---|---|
| Glycerin | 25% |
| Sorbitol (70%) | 15% |
| Water | 20% |
| Polishing Agent | 35% |
| Commercial Gum | 1% |
| Commercial Detergent | 1% |
| Peppermint Oil | 1% |
| Preservative | 0.1% |
| Stannous Fluoride | 0.4% |
| Saccharin | 0.4% |
| Other Ingredients | 1.1% |

The abrasive propeties of the polishing agent of the invention were studied and compared to the abrasive property of commercially available polishing agents. Calcium pyrophosphate abrasive was used as a reference standard and assigned an abrasivity index of 500. Compared with the reference standard, the abrasivity index obtained with polishing agents of this invention is listed in Table VIII below.

Table VIII

| Polishing Agent From | Abrasivity Index |
|---|---|
| Example I | 300 |
| Example II | 310 |
| Example III | 280 |
| Example IV | 420 |

As can be seen by examining the data in Table VIII, the abrasivity index of polishing agents of this invention is lower than reference standard phosphate of index value 500. Polishing agents of lower abrasive index are advantageous to have because they do not harm the tooth enamel and they are safe for human teeth when formulated into a tooth paste.

What is claimed is:

1. An oral dentifrice composition providing good cleaning and polishing of the teeth, comprising a polishing and abrasive ingredient, said polishing and abrasive ingredient comprising an amorphous precipitated silicon dioxide characterized as having a wet cake moisture of 66 to 76% inclusive, a structure index of from 200 to 354, an oil absorption of from 125 to 175 cc/100 grams; a void volume of from 2.55 to 4.0 cc Hg/gram $SiO_2$, and a BET surface area of from 80 to 200 square meters per gram; said silicon dioxide produced by a process comprising (1) forming an aqueous solution of an alkali metal silicate having a concentration of about 8 to 25% by weight and having a predetermined cumulative total of the said alkali metal silicate; said alkali metal silicate having the formula $M_2O(SiO_2)_X$, wherein M is an alkali metal selected from the group consisting of sodium and potassium, and X is from 2 to 4 inclusive; introducing a predetermined mol percentage of the said predetermined cumulative total of the said alkali metal silicate to a reaction vessel, said predetermined mol percentage comprising at least 8 mol percent and not more than 50 mol percent of said predetermined cumulative total of alkali metal silicate;

(2) continuously agitating said aqueous solution of said predetermined mol percentage of said alkali metal silicate in said reaction vessel;

(3) simultaneously adding the balance of said predetermined quantity of said alkali metal silicate to be employed in the reaction and an aqueous solution of a mineral acid selected from the group consisting of sulfuric acid, nitric acid and phosphoric acid, to the said agitated alkali metal silicate in the said reaction vessel at rates and concentrations so proportioned as to provide a controlled increase of effective alkalinity such that the maximum alkalinity produced upon the completion of the addition of the total quantity of said alkali metal silicate at the time of maximum alkalinity $t_m$ is from 20% to 500% higher than the initial alkalinity of the predetermined mol percentage of the cumulative total of the predetermined quantity of said alkali metal silicate to be employed in the reaction provided in the reaction vessel at the inception of the reaction;

(4) continuing the addition of said mineral acid after stopping the addition of said alkali metal silicate to a reaction mass pH of less than 6.0, said resulting reaction mass after all additions have been made thereto containing from 3 to 12% by weight of $SiO_2$ at the time of the completion of the reaction $t_f$, where $t_f$ is from 20 minutes to 4 hours, and the time to maximum alkalinity, $t_m$, is from 55% to 90% of $t_f$;

(5) maintaining the reaction temperature of said alkali metal silicate reaction mass between 50° and 90° C. throughout the reaction;

(6) filtering said reaction slurry; and (7) washing, drying, and milling said filtered mass, and recovering said silicon dioxide, when the said mol percentage initially charged to the reaction vessel is from 14 to 35%.

* * * * *

UNITED STATES PATENT AND TRADEMARK OFFICE
CERTIFICATE OF CORRECTION

PATENT NO. : 4,191,742
DATED : March 4, 1980
INVENTOR(S) : Satish K. Wason and Robert K. Mays It is certified that error appears in the above-identified patent and that said Letters Patent are hereby corrected as shown below:

Col. 1, line 48, "dentri-" should be -- denti- --.

Col. 2, line 29 and 32, "filter" should be -- filler --.

Col. 2, line 38, "or" should be -- of --.

Col. 2, line 46, "akali" should be -- alkali --.

Col. 5, line 20, following "that", -- they have -- should be inserted.

Col. 9, line 14, "and" should be omitted.

Col. 9, line 15, following "discovery", the word -- thereof -- should be inserted and "," should be omitted.

Col. 9, line 47, "mangnesium" should be -- magnesium --.

Col. 16, line 28, "mixture" should be -- mixer --.

Col. 17, line 2, "are" should be -- and --.

Signed and Sealed this

Twenty-fourth Day of June 1980

[SEAL]

Attest:

SIDNEY A. DIAMOND

Attesting Officer

Commissioner of Patents and Trademarks